United States Patent [19]
Mito

[11] Patent Number: 5,935,905
[45] Date of Patent: Aug. 10, 1999

[54] HERBICIDAL COMPOSITION

[75] Inventor: Nobuaki Mito, Kobe, Japan

[73] Assignee: Sumitomo Chemical Company, Limited, Osaka, Japan

[21] Appl. No.: 09/165,209

[22] Filed: Oct. 2, 1998

[30] Foreign Application Priority Data

Oct. 7, 1997 [JP] Japan ................................ 9-274365

[51] Int. Cl.$^6$ ................ A01N 57/02; A01N 43/653; A01N 33/04
[52] U.S. Cl. ............................. 504/128; 544/116
[58] Field of Search .............................. 504/128

[56] References Cited

U.S. PATENT DOCUMENTS

| | | |
|---|---|---|
| 4,030,909 | 6/1977 | Fischer ........................... 71/91 |
| 4,165,977 | 8/1979 | Fischer ........................... 71/91 |

FOREIGN PATENT DOCUMENTS 9002120  3/1990  WIPO .................. C07D 249/12

OTHER PUBLICATIONS

Dahman et al. (WPIDS, AN 98–194457, abstract of DE 19638887), 1998.
Dahman et al. (WPIDS, AN 98–160230, abstract of 19635060), 1996.
Balneaves, John M. (CA 119:111172, abstract of Plant Prot. Q. (1992), 7(4), 174–7), 1992.

*Primary Examiner*—Jose' G. Dees
*Assistant Examiner*—Sabiha N. Qazi
*Attorney, Agent, or Firm*—Birch, Stewart, Kolasch & Birch, LLP

[57] ABSTRACT

A herbicidal composition is described, which contains as active ingredients, ethyl 2-chloro-3-[2-chloro-4-fluoro-5-(4-difluoromethyl-4,5-dihydro-3-methyl-5-oxo 1H-1,2,4-triazol-1-yl)phenyl]propanoate; and N-(phosphonomethyl) glycine or a salt thereof. The herbicidal composition is useful for effective control of a wide variety of weeds in corn fields, soybean fields, wheat fields, barley fields, oat fields, rye fields, rice fields or paddy fields. Also described are a method for controlling weeds by foliar treatment with the above herbicidal composition; and use as a herbicide for foliar treatment, of a mixture of the above active ingredients.

3 Claims, No Drawings

HERBICIDAL COMPOSITION

TECHNICAL FIELD

The present invention relates to a herbicidal composition, and more particularly, it relates to a herbicidal composition for foliar treatment and a method for controlling weeds by foliar treatment of weeds therewith.

BACKGROUND ART

At the present time, numerous herbicides are commercially available and they are widely used. There are, however, many species of weeds to be controlled and their growth extends over a long time. For this reason, requested are herbicides with higher herbicidal activity, early appearance of the herbicidal effect, wide weed control spectrum, and safety to crops.

DISCLOSURE OF INVENTION

The present inventor has intensively studied to find out excellent herbicides. As a result, he has found that various weeds growing in crop lands or non-crop lands can be effectively controlled by applying a herbicidal composition containing as active ingredients, (a) ethyl 2-chloro-3-[2-chloro-4-fluoro-5-(4-difluoromethyl-4,5-dihydro-3-methyl-5-oxo-1H-1,2,4-triazol-1-yl)phenyl]propanoate (common name, carfentrazone-ethyl; hereinafter, referred to as carfentrazone-ethyl); and (b) N-(phosphonomethyl)glycine (common name, glyphosate; hereinafter, referred to as glyphosate) or a salt thereof.

He has further found that the herbicidal activity of the composition is synergistically increased as compared with the cases where the active ingredients are independently used, and the herbicidal composition can, therefore, be applied at a lower amount; and that the time for appearance of the herbicidal effect can be shortened, and that the weed control spectrum is expanded and a wide variety of weeds can be controlled, particularly in corn fields, soybean fields, wheat fields, barley fields, oat fields, rye fields, rice fields, and paddy fields, thereby completing the present invention.

Thus, the present invention provides a herbicidal composition comprising as active ingredients, carfentrazone-ethyl, and glyphosate or a salt thereof, (hereinafter referred to as the present composition); and a method for controlling weeds therewith.

MODE FOR CARRYING OUT THE INVENTION

Carfentrazone-ethyl, one of the active ingredients of the present composition is a compound as described in AG CHEM NEW COMPOUND REVIEW, VOLUME 15, 1997 (published by AG CHEM INFORMATION SERVICES, 1997), page 21.

Glyphosate, another one of the active ingredients of the present composition is a compound as described in Farm Chemicals Handbook, 1995 (published by Meister, Publishing Co., 1995), page C188. In the present invention, "salts" mean all agrochemically acceptable salts.

The present composition has a herbicidal activity to a wide variety of weeds with crop selectivity. The present composition exhibits excellent herbicidal effect in agricultural or horticultural fields such as conventional tillage cultivation fields, non-tillage cultivation fields and orchard, and in non-crop lands such as play fields, sports fields, vacant lots, forestry, railroads, roadsides, electric utility and right-of-ways. Therefore, the present composition is excellent as a herbicidal composition.

The present composition effectively controls the main weeds in corn fields, soybean fields, wheat fields, barley fields, oat fields, rye fields or rice fields, e.g., dicotyledonous plants such as wild buckwheat (*Polygonum convolvulus*), pale smartweed (*Polygonum lapathifolium*), Pennsylvania smartweed (*Polygonum pensylvanicum*), common purslane (*Portulaca oleracea*), common lambsquarters (*Chenopodium album*), redroot pigweed (*Amaranthus retroflexus*), wild mustard (*Sinapis arvensis*), hemp sesbania (*Sesbania exaltata*), sicklepod (*Cassia obtusifolia*), velvetleaf (*Abutilon theophrasti*), prickly sida (*Sida spinosa*), ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa* L.), jimsonweed (*Datura stramonium*), black nightshade (*Solanum nigrum*), common cocklebur (*Xanthium strumarium*), common sunflower (*Helianthus annuus*), field bindweed (*Convolvulus arvensis*), sun spurge (*Euphorbia helioscopia*), devils beggarticks (*Bidens frondosa*), common ragweed (*Ambrosia artemisiifolia*), giant ragweed (*Ambrosia trifida*), catchweed bedstraw (*Galium aparine*) Ivyleaf speedwell (*Veronica hederifolia*), kochia (*Kochia scoparia*) field pansy (*Viola arvensis*), persian speedwell (*Veronica persica*), canada thistle (*Crisium arvense*), common chickweed (*Stellariamedia*), purple deadnettle (*Lamium purpureum*), henbit (*Lamium amplexicaure*), common poppy (*Papaver rhoeas*), scentless chamomile (*Matricaria perforata*), pineappleweed (*Matricaria matricarioides*), and Mare'stail (*Erigeron canadensis*); and monocotyledonous plants such as barnyardgrass (*Echinochloa crus-galli*), green foxtail (*Setaria viridis*), giant foxtail (*Setaria faberi*), yellow foxtail (*Setaria glauca*), southern crabgrass (*Digitaria ciliaris*), goosegrass (*Eleusine indica*), johnsongrass (*Sorghum halepense*), quackgrass (*Agropyron repens*), shattercane (*Sorghum bicolor*), amazon sprangletop (*Leptochloa panicoides*), red sprangletop (*Leptochloa filiformis*), broadleaf signalgrass (*Brachiaria platyphylla*), umbrella sedge (*Cyperus difformis*), and rice flatsedge (*Cyperus iria*), while it exhibits no significant phytotoxicity on crops such as corn, soybean, wheat, barley, oat, rye and rice.

When the present composition is used in paddy fields, it may be applied to foliage of weeds before flooding, preferably.

The present composition effectively controls weeds in paddy fields, e.g., dicotyledonous plants such as hemp sesbania (*Sesbania exaltata*), ivyleaf morningglory (*Ipomoea hederacea*), tall morningglory (*Pharbitis purpurea*), entireleaf morningglory (*Ipomoea hederacea* var. *integriuscula*), pitted morningglory (*Ipomoea lacunosa* L.), common cocklebur (*Xanthium pensylvanicum*), and pensylvania smartweed (*Polygonum pensylvanicum*); and monocotyledonous plants such as barnyardgrass (*Echinochloa crus-galli*), southern crabgrass (*Digitaria ciliaris*), goosegrass (*Eleusine indica*), amazon sprangletop (*Leptochloa panicoides*), red sprangletop (*Leptochloa filiformis*), broadleaf signalgrass (*Brachiaria platyphylla*), umbrella sedge (*Cyperus difformis*), and rice flatsedge (*Cyperus iria*), while it exhibits no significant phytotoxicity on rice.

Crops will be understood as meaning also those crops that have been made tolerant to herbicides or classes of herbicides by conventional breeding or genetic engineering methods e.g. to glyphosate.

Crops of cultivated plants which are tolerant to glyphosate are preferably prepared by biotechnological methods. The methods for the preparation of such plants which are tolerant to glyphosate are described in detail in the International Patent Application WO 92/04449, WO 92/19719 and WO 92/00377, and U.S. Pat. Nos.5,188,642, 4,971,908, 5,145,783,5,510,471 and 5,633,448.

In the present composition, the mixing ratio of carfentrazone-ethyl to glyphosate or a salt thereof, although it may vary with the species of weeds to be controlled, situation and conditions of application, and other factors, is usually in the range of 1:5 to 500 by weight.

The present composition may be usually used in the form of formulations such as emulsifiable concentrates, wettable powders, flowables, or granules which can be prepared by mixing the composition with solid carriers, liquid carriers, or other bulking agents, and if necessary, adding surfactants or other adjuvants to this mixture. In such a formulation, carfentrazone-ethyl and glyphosate or a salt thereof are usually contained at the total amount of 0.5 to 90 wt %, preferably 1 to 80 wt %.

The solid carrier to be used in the formulation may include, for example, the following materials in fine powder or granule form: clays (e.g., kaolinite, diatomaceous earth, synthetic hydrated silicon oxide, Fubasami clay, bentonite, acid clay); talc and other inorganic minerals (e.g., sericite, powdered quartz, powdered sulfur, activated carbon, calcium carbonate); and chemical fertilizers (e.g., ammonium sulfate, ammonium phosphate, ammonium nitrate, ammonium chloride, urea). The liquid carrier may include, for example, water; alcohols (e.g., methanol, ethanol); ketones (e.g., acetone, methyl ethyl ketone, cyclohexanone); aromatic hydrocarbons (e.g., toluene, xylene, ethylbenzene, methylnaphthalene); non-aromatic hydrocarbons (e.g., hexane, cyclohexane, kerosine); esters (e.g., ethyl acetate, butyl acetate); nitriles (e.g., acetonitrile, isobutyronitrile); ethers (e.g., dioxane, diisopropyl ether); acid amides (e.g., dimethylformamide, dimethylacetamide); and halogenated hydrocarbons (e.g., dichloroethane, trichloroethylene).

The surfactant may include, for example, alkylsulfate esters; alkylsulfonate salts; alkylarylsulfonate salts; alkyl aryl ethers and their polyoxyethylene derivatives; polyethylene glycol ethers; polyhydric alcohol esters; and sugar alcohol derivatives.

The other adjuvants may include, for example, adhesive agents and dispersing agents, such as casein, gelatin, polysaccharides (e.g., powdered starch, gum arabic, cellulose derivatives, alginic acid), lignin derivatives, bentonite, and synthetic water-soluble polymers (e.g., polyvinyl alcohol, polyvinyl pyrrolidone, polyacrylic acid); and stabilizers such as PAP (isopropyl acid phosphate), BHT (2,6-di-tert-butyl-4-methylphenol), BHA (2-/3-tert-butyl-4-methyoxyphenol), vegetable oils, mineral oils, fatty acids, and fatty acid esters.

The present composition can also be prepared by making the active ingredients into the respective formulations using the above formulation technique and then mixing these formulations.

The present composition thus formulated may be applied to plants as such, or after diluted with water or the like. The present composition may also be used in admixture with other herbicides, in which case the herbicidal activity can be expected to be enhanced. The present composition after diluted with water may also be used in admixture with adjuvants, in which case the herbicidal activity can be expected to be enhanced. The present composition can also be used together with insecticides, bactericides, fungicides, plant growth regulators, fertilizers, soil conditioners, safeners or other agents.

The application amount of the present composition, although it may vary with the mixing ratio of carfentrazone-ethyl to glyphosate or a salt thereof as the active ingredient compounds, weather conditions, formulation types, application timing, application methods, application places, weeds to be controlled, and crops to be protected, is usually in the range of 100 to 4000 g, preferably 500 to 1000 g, as the total amount of active ingredient compounds per hectare. In the case of emulsifiable concentrates, wettable powders, flowables, or other similar formulations, they are usually applied after diluted in their prescribed amounts with water at a ratio of 100 to 1000 liters per hectare.

The following will describe formulation examples, in which parts are by weight.

FORMULATION EXAMPLE 1

One part of carfentrazone-ethyl, 25 parts of glyphosate or a salt thereof, 3 parts of calcium lignin sulfonate, 2 parts of sodium laurylsulfate, and 69 parts of synthetic hydrated silicon oxide are well pulverized and mixed to give each wettable powder.

FORMULATION EXAMPLE 2

0.4 part of carfentrazone-ethyl, 40 parts of glyphosate or a salt thereof, 3 parts of calcium lignin sulfonate, 2 parts of sodium laurylsulfate, and 54.6 parts of synthetic hydrated silicon oxide are well pulverized and mixed to give each wettable powder.

FORMULATION EXAMPLE 3

Ten parts of carfentrazone-ethyl, 40 parts of glyphosate or a salt thereof, 3 parts of calcium lignin sulfonate, 2 parts of sodium laurylsulfate, and 45 parts of synthetic hydrated silicon oxide are well pulverized and mixed to give each wettable powder.

FORMULATION EXAMPLE 4

0.5 part of carfentrazone-ethyl, 10 parts of glyphosate or a salt thereof, 3 parts of calcium lignin sulfonate, 2 parts of sodium laurylsulfate, and 84.5 parts of synthetic hydrated silicon oxide are well pulverized and mixed to give each wettable powder.

FORMULATION EXAMPLE 5

One part of carfentrazone-ethyl, 25 parts of glyphosate or a salt thereof, 3 parts of polyoxyethylene sorbitan monooleate, 3 parts of CMC (carboxymethylcellulose), and 68 parts of water are mixed and wet pulverized until the particle size comes to 5 microns or smaller to give each flowable.

FORMULATION EXAMPLE 6

0.4 part of carfentrazone-ethyl, 40 parts of glyphosate or a salt thereof, 3 parts of polyoxyethylene sorbitan monooleate, 3 parts of CMC (carboxymethylcellulose), and 53.6 parts of water are mixed and wet pulverized until the particle size comes to 5 microns or smaller to give each flowable.

FORMULATION EXAMPLE 7

10 parts of carfentrazone-ethyl, 40 parts of glyphosate or a salt thereof, 3 parts of polyoxyethylene sorbitan monooleate, 3 parts of CMC (carboxymethylcellulose), and 44 parts of water are mixed and wet pulverized until the particle size comes to 5 microns or smaller to give each flowable.

FORMULATION EXAMPLE 8

0.5 part of carfentrazone-ethyl, 10 parts of glyphosate or a salt thereof, 3 parts of polyoxyethylene sorbitan monooleate, 3 parts of CMC (carboxymethylcellulose), and 83.5 parts of water are mixed and wet pulverized until the particle size comes to 5 microns or smaller to give each flowable.

The following will describe a test example.

Evaluation Criteria

The herbicidal activity is evaluated at 11 levels with indices of 0 to 10, i.e., shown by numeral "0", "1", "2", "3", "4", "5", "6", "7", "8", "9", or "10", wherein "10" means that there was no or little difference in the degree of germination or growth between the treated plants and the untreated plants at the time of evaluation, and "10" means that the test plants died completely or their germination or growth was completely inhibited. The herbicidal activity is excellent when ranked at "7", "8", "9", or "10", but insufficient when ranked at as "6", or lower.

TEST EXAMPLE 1

Plastic pots each having an area of 26.5×19 cm$^2$ and a depth of 7 cm were filled with upland soil, and then seeded with giant foxtail (*Setaria faberi*), barnyardgrass (*Echinochloa crus-galli*), southern crabgrass (*Digitaria ciliaris*), common lambsquarters (*Chenopodium album*), common ragweed (*Ambrosia artemisiifolia*), common cocklebur (*Xanthium strumarium*) and ivyleaf morningglory (*Ipomoea hederacea*). In a green house, common lambsquarters and common ragweed were grown for 28 days, Common cocklebur, ivyleaf morningglory, giant foxtail, and southern crabgrass were grown for 21 days, and barnyardgrass was grown for 14 days, respectively.

An emulsifiable concentrate of carfentrazone-ethyl, which had been obtained by well mixing 10 parts of carfentrazone-ethyl, 14 parts of polyoxyethylene styryl phenyl ether, 6 parts of calcium dodecylbenzenesulfonate, 35 parts of xylene, and 35 parts of cyclohexanone, a formulation product of glyphosate (trade name, Roundup; seller, Monsant Japan Limited; distributor, Sankyo Co., Ltd.; it comprises glyphosate isopropylamine salt), and a mixture of the emulsifiable concentrate of carfentrazone-ethyl and the formulation product of glyphosate were independently diluted in their prescribed amounts with water. Each dilution was uniformly sprayed over the test plants with a small sprayer. After the application, the test plants were grown in the greenhouse for 4 days, and the herbicidal activity was then examined. The results are shown in Table 1.

TABLE 1

| Compound | Dosage (g/ha) | G | B | S | L | R | C | I |
| --- | --- | --- | --- | --- | --- | --- | --- | --- |
| Carfentrazone-ethyl | 20 | 3 | 3 | 2 | 6 | 6 | 6 | 6 |
| Glyphosate isopropylamine salt | 500 | 2 | 2 | 1 | 1 | 1 | 1 | 1 |
| Carfentrazone-ethyl + Glyphosate isopropylamine salt | 20 + 500 | 8 | 7 | 9 | 9 | 9 | 10 | 10 |

Note: Signals in TABLE 1 mean as follows.
G: giant foxtail
B: barnyardgrass
S: southern crabgrass
L: common lambsquarters
R: common ragweed
C: common cocklebur
I: ivyleaf morningglory The effect of the present invention A wide variety of weeds in corn fields, soybean fields, wheat fields, barley fields, oat fields, rye fields, rice fields or paddy fields, can be effectively controlled by the present composition.

I claim:

1. A herbicidal composition comprising as active ingredients, (a) ethyl 2-chloro-3-[2-chloro-4-fluoro-5-(4-difluoromethyl-4,5-dihydro-3-methyl-5-oxo-1H-1,2,4-triazol-1-yl)phenyl]propanoate; and (b) N-(phosphonomethyl)glycine or a salt thereof.

2. The herbicidal composition according to claim 1, wherein the weight ratio of component (a) to component (b) is 1:5 to 500.

3. A method for controlling weeds comprising applying an effective amount of the composition according to claim 1 or 2 to weeds by foliar treatment.

* * * * *

(12) REEXAMINATION CERTIFICATE (4713rd)
United States Patent
Mito

(10) Number: US 5,935,905 C1
(45) Certificate Issued: Jan. 7, 2003

(54) HERBICIDAL COMPOSITION

(75) Inventor: Nobuaki Mito, Kobe (JP)

(73) Assignee: Sumitomo Chemical Company, Limited, Osaka (JP)

Reexamination Request:
No. 90/005,869, May 10, 2000

Reexamination Certificate for:
Patent No.: 5,935,905
Issued: Aug. 10, 1999
Appl. No.: 09/165,209
Filed: Oct. 2, 1998

(30) Foreign Application Priority Data

Oct. 7, 1997 (JP) .............................................. 9-274365

(51) Int. Cl.$^7$ ...................... A01N 57/02; A01N 43/653; A01N 33/04
(52) U.S. Cl. ........................................ 504/128; 504/116
(58) Field of Search ......................................... 504/128

(56) References Cited

U.S. PATENT DOCUMENTS 5,968,873 A * 10/1999 Dahmen et al. ............ 504/128

OTHER PUBLICATIONS

Lee et al, Evaluation of Carfentrazone–Ethyl, Aug. 1997, 16th Asian–Pacific Weed Science Society Conference, Session 6A, pp. 256–261.*

Lee et al, Evaluation of Carfentrazone–ethyl, 16th Asian–Pacific Wee Science Society Conference, Session 6A, pp. 306–309, 1997.*

Lee et al, Evaluation of Carfentrazone–ethyl, Kor. J. Weed Sci., 17(3), pp. 356–361, 1997.*

* cited by examiner

*Primary Examiner*—Alton Pryor

(57) ABSTRACT

A herbicidal composition is described, which contains as active ingredients, ethyl 2-chloro-3-[2-chloro-4-fluoro-5-(4-difluoromethyl-4,5-dihydro-3-methyl-5-oxo 1H-1,2,4-triazol-l-yl)phenyl]propanoate; and N-(phosphonomethyl) glycine or a salt thereof. The herbicidal composition is useful for effective control of a wide variety of weeds in corn fields, soybean fields, wheat fields, barley fields, oat fields, rye fields, rice fields or paddy fields. Also described are a method for controlling weeds by foliar treatment with the above herbicidal composition; and use as a herbicide for foliar treatment, of a mixture of the above active ingredients.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–3 are cancelled.

New claims 4–14 are added and determined to be patentable.

*4. A method for controlling weeds which comprises applying by foliar treatment an effective amount of a herbicidal composition comprising active ingredients consisting essentially of,*

(*a*) *ethyl 2-chloro-3-(2-chloro-4-fluoro-5-(4-difluoromethyl-4,5-dihydro-3-methyl-5-oxo-1H-1,2,4-triazol-1-yl)phenyl)propanote; and*

(*b*) *N-(phosphonomethyl)glycine or a salt thereof,*

*to weeds in a field selected from the group consisting of a corn field, wheat field, barley field, oat field and rye field;*

*wherein the ratio of (a)/(b) is from 1:5 to 500; and the herbicidal composition does not exhitit significant phytotoxicity against the corn, wheat, barley, oat or rye crops.*

*5. The method according to claim 4, wherein the field is a cornfield.*

*6. The method according to claim 5, wherein the cornfield is a non-tillage cultivation field.*

*7. The method according to claim 4, wherein the field is a wheat field, barley field, oat field or rye field.*

*8. The method according to claim 7, wherein the wheat field, barley field, oat field or rye field is a non-tillage cultivation field.*

*9. The method according to claim 4, wherein the weed is giant foxtail, barnyardgrass, southern crabgrass, common lambsquarters, common ragweed, common cocklebur or ivyleaf morningglory.*

*10. The method according to claim 4, wherein the weed is ivyleaf morningglory.*

*11. The method according to claim 5, wherein the weed is ivyleaf morningglory.*

*12. The method for controlling weeds according to claim 4, wherein said herbicidal composition contains a solid carrier.*

*13. The method for controlling weeds according to claim 4, wherein said herbicidal composition contains a liquid carrier.*

*14. The method for controlling weeds according to claim 4, wherein said herbicidal composition contains a surfactant.*

\* \* \* \* \*